United States Patent [19]

Redmon et al.

[11] Patent Number: 6,161,536
[45] Date of Patent: Dec. 19, 2000

[54] DOSAGE FORM FOR AEROSOL ADMINISTRATION

[75] Inventors: Martin P. Redmon, Marlborough; Joseph A. West, Mansfield, both of Mass.

[73] Assignee: Sepracor Inc., Marlborough, Mass.

[21] Appl. No.: 09/168,216

[22] Filed: Oct. 7, 1998

Related U.S. Application Data

[60] Provisional application No. 60/061,363, Oct. 8, 1997.

[51] Int. Cl.⁷ .................................................. A61M 11/00
[52] U.S. Cl. .............................. 128/200.14; 128/200.16; 128/203.12
[58] Field of Search ........................ 128/200.14, 203.12, 128/200.16, 203.21

[56] References Cited

U.S. PATENT DOCUMENTS

| | | | |
|---|---|---|---|
| 3,898,338 | 8/1975 | Martin et al. | 424/250 |
| 4,089,432 | 5/1978 | Crankshaw et al. | 215/6 |
| 4,194,640 | 3/1980 | Crankshaw et al. | 215/6 |
| 4,258,845 | 3/1981 | Potts | 206/221 |
| 4,267,925 | 5/1981 | Crankshaw et al. | 206/221 |
| 4,274,543 | 6/1981 | Braymer, Jr. et al. | 215/6 |
| 4,331,233 | 5/1982 | Braymer, Jr. | 206/221 |
| 4,371,516 | 2/1983 | Gregory et al. | 424/22 |
| 5,215,079 | 6/1993 | Fine et al. | 128/200.14 |
| 5,586,550 | 12/1996 | Ivri et al. | 128/200.16 |

FOREIGN PATENT DOCUMENTS

| | | | |
|---|---|---|---|
| 0651997 | 5/1995 | European Pat. Off. | A61K 9/20 |
| WO 9735882 | 10/1997 | WIPO | C07K 14/785 |

*Primary Examiner*—Michael A. Brown
*Assistant Examiner*—Lalita M. Hamilton
*Attorney, Agent, or Firm*—Heslin & Rothenberg, P.C.

[57] ABSTRACT

A method for preparing aerosols of water-sensitive medicaments and a pharmaceutical kit for aerosol administration are disclosed. The kit includes (a) a solid state open matrix network of a medicament in a first container; and (b) an aqueous vehicle in a second container. The first and second containers may be separate or they may be chambers within a single housing. The solid state network may be a unit dose of medicament, and the quantity of aqueous vehicle will then be that quantity needed to deliver one unit dose by aerosol; alternatively, the solid state network may contain a plurality of unit doses of medicament, in which case the quantity of aqueous vehicle will be that quantity needed to deliver the number of unit doses in the network. The kit may also include a metered dose nebulizer. A preferred medicament for use in the method is formoterol.

22 Claims, 3 Drawing Sheets

DOSAGE FORM FOR AEROSOL ADMINISTRATION

CROSS REFERENCE TO RELATED APPLICATION

This application claims priority of U.S. Provisional Application 60/061,363 filed October 8, 1997.

FIELD OF THE INVENTION

This invention relates to the delivery of therapeutic liquids to the respiratory system.

BACKGROUND OF THE INVENTION

Aerosol formulations are employed in respiratory therapy for the topical administration of medication to the mucosal linings of the tracheobronchial tree. The term aerosol describes a nebulized solution consisting of very fine particles carried by a gas (usually air) to the site of therapeutic application. When the site of application is the alveoli and small bronchioles, the medicament must be dispersed as droplets of roughly 5 micron diameter. When the target is the nasal and pharyngeal region, larger droplets are appropriate. Conditions susceptible to treatment with aerosols include bronchospasms, loss of compliance, mucosal edema, pulmonary infections and the like.

Solutions of medicament in buffered saline and similar vehicles are commonly employed to generate an aerosol in a nebulizer. Within the container of a conventional air-driven nebulizer is a small unit that produces aerosolized droplets inside the flask. The walls of the flask act as a baffle removing large droplets from the mist. The large droplets run down the wall and drop back into the reservoir, leaving a mist of small droplets that can penetrate into the lung. A current of air or oxygen carries the fine mist through the large outlet tube of the nebulizer. Simple nebulizers operate on Bernoulli's principle and employ a stream of air or oxygen to generate the spray particles. More complex nebulizers employ ultrasound to create the spray particles. Both types are well known in the art and are described in standard textbooks of pharmacy such as Sprowls'American Pharmacy and Remington's The Science and Practice of Pharmacy. Other devices for generating aerosols employ compressed gases, usually hydrofluorocarbons and chlorofluorocarbons, which are mixed with the medicament and any necessary excipients in a pressurized container; these devices are likewise described in standard textbooks such as Sprowls and Remington. Because all nebulizers require a fluid medium for the development of the aerosol spray, and because the spray is to be inspired directly into the lung, water is the only vehicle that can reasonably be employed. A problem thus arises when the medicament is itself not sufficiently stable in an aqueous environment to provide a practical shelf life for the aqueous formulation.

Various methods have been tried to circumvent this problem. It is known in the art to prepare and maintain the aqueous solution or suspension at a reduced temperature. This approach has two drawbacks: first, storage becomes expensive and bothersome; and second, the degradative processes are slowed, but they are not stopped.

An alternative to refrigerating a solution or suspension that has already been prepared is to make up the medicament solution immediately before use. However, the accurate and sterile transfer of the medicament into the carrier is generally only practical when the medicament is provided as a solution in another (non-aqueous) solvent. The formulations chemist is then faced with the problem of devising not just one, but two stable, compatible formulations.

Therefore, it would be highly desirable to have a system for generating water-based aerosols from water-sensitive medicaments without the need for refrigeration. This need is satisfied, the limitations of the prior art overcome, and other benefits realized in accordance with the principles of the present invention.

SUMMARY OF THE INVENTION

In one aspect, the invention relates to a pharmaceutical kit for aerosol administration. In one embodiment the kit comprises (a) a solid state open matrix network of a medicament and a pharmaceutically acceptable water soluble or water-dispersible carrier material contained within a first substantially water-impermeable container; and (b) a sufficient quantity of an aqueous vehicle to dissolve the matrix network within fifteen seconds contained within a second substantially water-impermeable container. The first and second containers may be separate or they may be chambers within a single housing. The solid state network may be a unit dose of medicament, and the quantity of aqueous vehicle will then be that quantity needed to deliver one unit dose by nebulization; alternatively, the solid state network may contain a plurality of unit doses of medicament, in which case the quantity of aqueous vehicle will be that quantity needed to deliver the number of unit doses in the network. The kit may also include a metered dose nebulizer.

In another embodiment of the kit aspect, the kit may comprise a solid state open matrix network of a medicament and a pharmaceutically acceptable water soluble or water-dispersible carrier material contained within a nebulizer reservoir and enclosed by a substantially water-impermeable seal. The seal will be penetrated or removed by the patient prior to using the nebulizer, and an aqueous vehicle will be added. As before, the solid state network may contain one or a plurality of unit doses of the medicament.

In another aspect, the invention relates to a method for preparing a formulation for nebulization. The method comprises: (a) providing a solid state open matrix network of a medicament and a pharmaceutically acceptable water soluble or water-dispersible carrier material; and (b) combining the matrix network with a sufficient quantity of an aqueous vehicle to dissolve the matrix network within fifteen seconds. In a closely related method aspect, the aqueous solution from (b) is converted to an aerosol by nebulization. The solution may be converted to an aerosol by a conventional nebulizer or by a metered dose nebulizer.

In another aspect, the invention relates to a method for providing a water-sensitive medicament for administration as a nebulized aqueous aerosol. The method comprises: (a) dissolving or suspending a water-sensitive medicament and a pharmaceutically acceptable water soluble or water-dispersible carrier material in a vehicle; (b) introducing the medicament and vehicle into a reservoir for a nebulizer; (c) freezing the medicament and the vehicle in the reservoir and (d) lyophilizing. The method provides a solid state open matrix network of the medicament in the reservoir, ready to use simply by adding vehicle. Alternatively, the medicament and carrier in vehicle may be lyophilized and then transferred into the reservoir.

In preferred embodiments of all of the above aspects, the medicament is formoterol or a salt thereof. A particularly preferred medicament is R,R-formoterol, and a particularly preferred salt is R,R-formoterol-L-tartrate. The pharmaceutically acceptable water soluble or water-dispersible carrier material is a protein, polypeptide or polysaccharide, preferably gelatin, alginate or dextran.

BRIEF DESCRIPTION OF THE DRAWINGS

The invention may be best understood by reference to the detailed description of the preferred embodiments herein when read in conjunction with drawings in which.

DETAILED DESCRIPTION OF THE INVENTION

Figure 1:
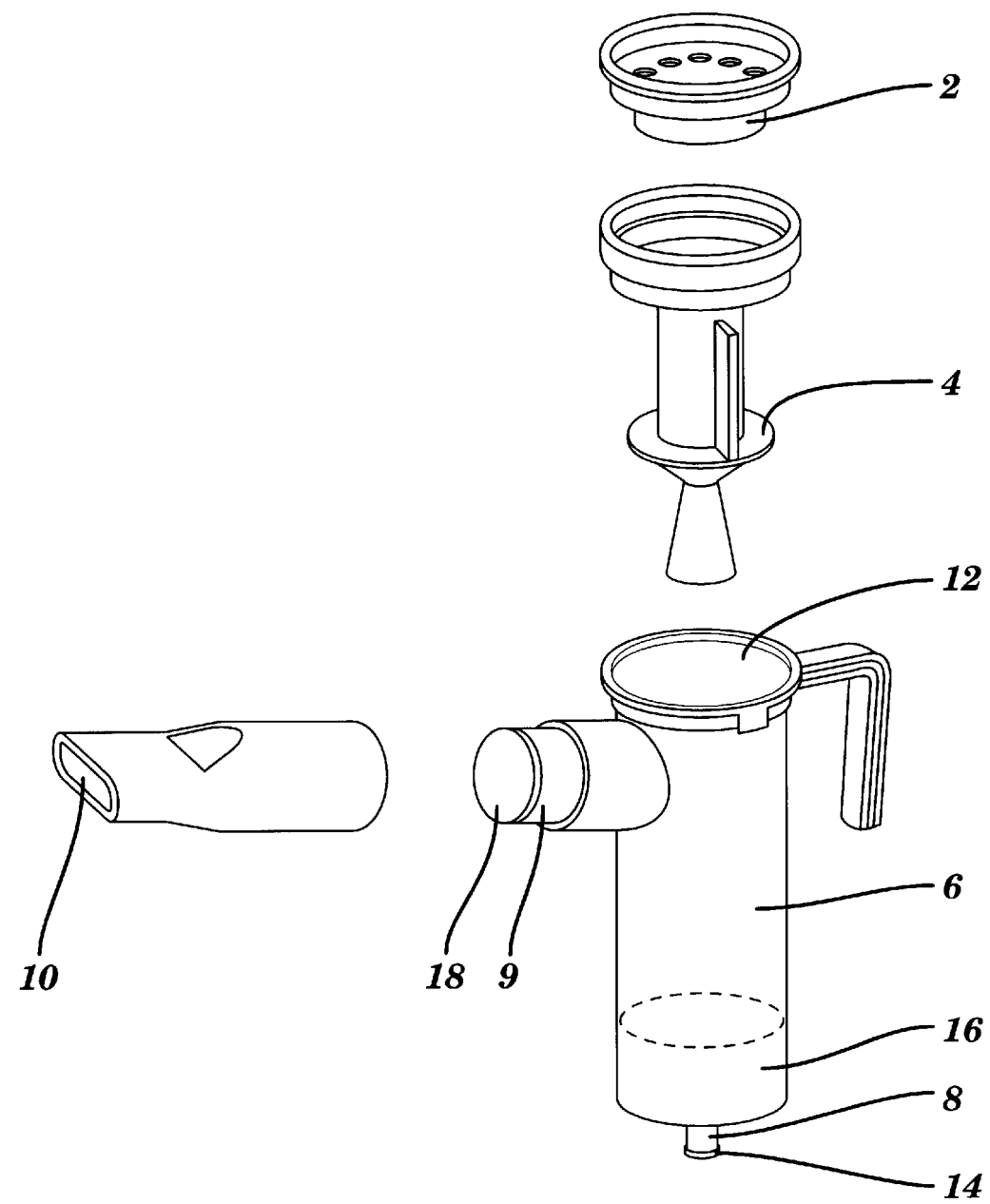
FIG. 1 depicts an unassembled perspective view of the components that make up a nebulizer device, showing the deposition of a matrix according to the principles of the present invention.
Figure 2:
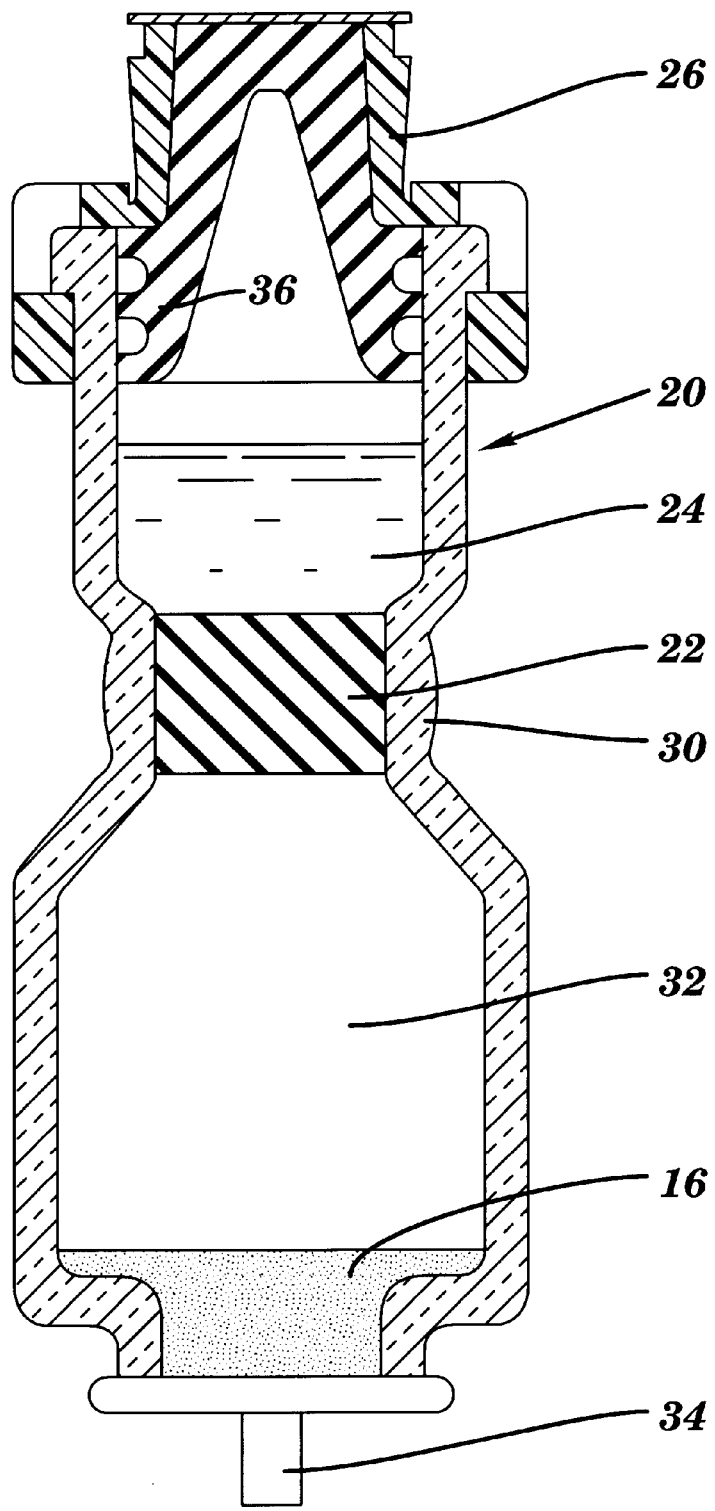
FIG. 2 depicts a cross-sectional schematic representation of a two-chambered container having a matrix deposited therein in accordance with the principles of the present invention.
Figure 3:
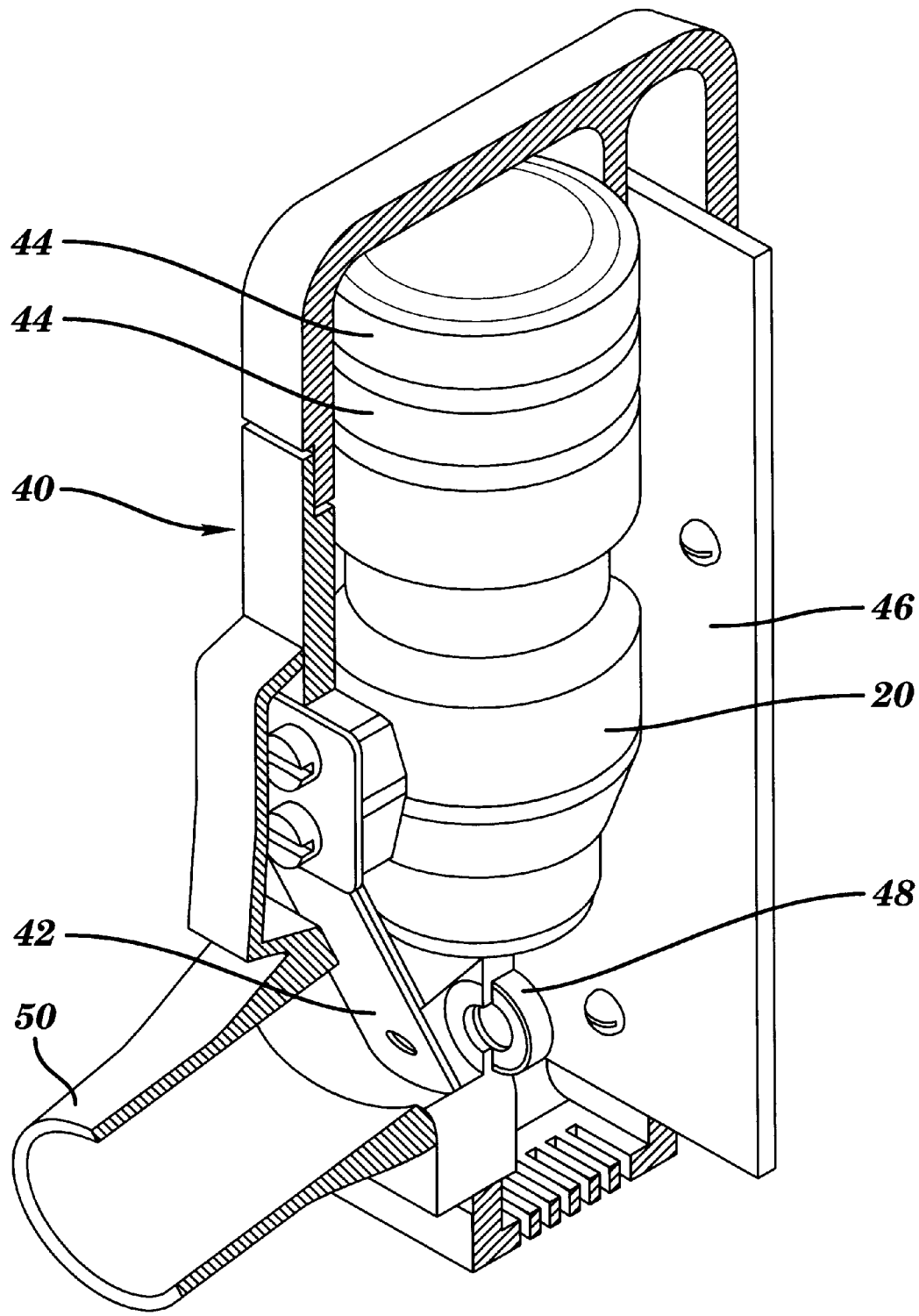
FIG. 3 depicts a sectional representation of a metered close nebulizer, showing the operational positioning of the container of FIG. 2

The common feature that links all of the aspects of the invention is the use of a solid state open matrix network of a medicament to quickly generate a precisely controlled volume of an aqueous solution suitable for aerosol administration. The precise measurement of very small amounts of solids is difficult and homogeneity becomes critical when small amounts of highly potent agents are to be dispensed. The invention provides a particular advantage in the manufacture of dosage forms for aerosol administration in that it enables the manufacturer to precisely meter a solution (prior to lyophilization) rather than having to weigh or otherwise measure a powder. Additionally, the use of the solid phase matrix in the various embodiments of the invention allows an individual patient to make up a sterile aerosol solution accurately, immediately before use and without the involvement of a health care professional. Accuracy and sterility are both important considerations in inhalation therapy.

The invention employs a pharmaceutical dosage form which can be rapidly disintegrated by water. By "rapidly disintegrated" is meant that the solid state matrices are disintegrated in water within 15 seconds. Preferably the solid state matrix disintegrates (dissolves or disperses) within 10 seconds or less. The disintegration time is measured by a procedure analogous to the Disintegration Test for Tablets, USP XXII, Dissolution <711>, p. 1578–1579 (1990). The procedure is as follows:

A glass or suitable plastic tube 80 to 100 mm long, with an internal diameter of about 28 mm and an external diameter of 30 to 31 mm, is fitted at the lower end, so as to form a basket, with a disc of rustproof wire gauze complying with the requirements for a No. 1.70 sieve. The basket is suspended centrally in a glass or plastic cylinder having a flat base and an internal diameter of about 45 mm. The cylinder contains water 15 cm deep at a temperature between 36° and 38° C. The basket is raised and lowered repeatedly in such a manner that the complete up and down movement is repeated thirty times a minute. At the highest position the gauze just breaks the surface of the water and at the lowest position the upper rim of the basket just remains clear of the water. Place the solid state matrix in the basket and raise and lower it. The solid state matrices are disintegrated when no particle remains above the gauze which would not readily pass through it. No such particle should remain after 15 seconds.

By the term "open matrix network" there is meant a network of water-soluble or water-dispersible carrier material having dispersed interstices. The open matrix network of carrier material is of generally low density. The density will generally be within the range of 10 to 200 mg/cc, and most commonly 30 to 60 mg/cc. The density of the solid state matrix is affected by the amount of medicament or additive incorporated, and may on occasion fall outside the above mentioned preferred limits. The open matrix network, which is similar in structure to a solid, open-cell foam, enables the aqueous vehicle to enter the product through the interstices and permeate through the interior. Permeation by aqueous media exposes the carrier material of both the interior and exterior of the product to the action of the aqueous medium, whereby the network of carrier material is rapidly disintegrated.

The carrier material used in the product of the invention nay be any water-soluble or water-dispersible material that is pharmacologically acceptable or inert to the medicament and which is capable of forming a rapidly disintegratable open matrix network. Use of a water-soluble material as the carrier results in the most rapid disintegration of the matrix when the product is placed in an aqueous medium. A particularly advantageous carrier may be formed from a protein such as gelatin, particularly partially hydrolyzed gelatin. The hydrolyzed gelatin is preferably used at concentrations of about 1 to 6% weight/volume based on the volume of the initial solution, prior to lyophilization. Other carrier materials include polysaccharides such as hydrolyzed dextran, dextrin and alginates (e.g. sodium alginate) or mixtures of above mentioned carriers with each other or with other carrier materials such as polyvinyl alcohol, polyvinylpyrrolidine or acacia. The solid state matrices of the present invention may incorporate ingredients in addition to the medicament, for example coloring agents, flavoring agents, preservatives (e.g. bacteriostatic agents), and the like.

The solid state matrices of the present invention are prepared by subliming (lyophilizing) solvent (usually water) from a composition comprising the medicament and a solution of the carrier material in a solvent, the composition being in the solid state in a mold, which can be a reservoir for a nebulizer. Although the solvent is primarily water, it may contain a co-solvent such as t-butanol when necessary to improve the solubility of the medicament. The composition may also contain a surfactant e.g. Tween 90 [polyoxyethylene (20) sorbitan-mono-oleate] to aid in the dispersion of the medicament.

The mold may be in the form of a tray having a series of cylindrical or other shape depressions in it, each of a size corresponding to the desired size of the solid state matrix. Alternatively, the size of the depression may be larger than the desired size of the article and, after the contents have been freeze dried, the product can be cut into the desired size (for example thin wafers). In one embodiment the mold comprises an aluminum film containing one or more depressions. In another embodiment, the mold is a body (usually plastic) suitable for use as a reservoir for a nebulizer. The mold is cooled, a predetermined amount of water containing the carrier material, the medicament and any other desired ingredient is introduced into the mold, frozen, and subjected to reduced pressure. The freeze dried products may then be removed from the mold and stored, protected from moisture, or the freeze dried products may be left in the mold and the mold may be sealed with a moisture-impermeable, pealable overwrap. If the freeze drying has been (carried out in a nebulizer reservoir, the reservoir can be sealed with a moisture-impermeable seal as discussed below. Alternatively, the matrices may be taken from a mold and placed in a reservoir, which is then sealed with the moisture impermeable seal.

The following examples illustrate the preparation of the matrix:

EXAMPLE 1

A hydrolyzed gelatin solution is prepared by dissolving 30 g of gelatin in 1L of water and heating at 121° C. at 1.03 bar for one hour. The solution is allowed to cool to room temperature. One gram of R,R-formoterol-L-tartrate is dissolved in the solution. A mold in the form of an aluminum film containing 75 cylindrical depressions (each depression being about 0.5 cm diameter and 1 cm deep) is cooled to about −192° C. in liquid nitrogen contained in a stainless steel tray. One half milliliter of the mixture is introduced into each depression and frozen. The mold is placed in a vacuum chamber at room temperature and a vacuum of 0.3 mm Hg is applied for 12 hours. The freeze dried matrices, each containing 0.5 mg of formoterol tartrate (about 10 to 20 unit doses), are covered with a pealable aluminum seal.

The amount of R,R-formoterol-L-tartrate dissolved in the hydrolyzed gelatin solution can be varied to provide unit doses rather than multiple doses. When a unit dose (e.g. 50 µg) is desired, one would use 100 mg/L rather than the 1 g/L described. Reasonable limits for R,R-formoterol-L-tartrate are between 6 mg/L and 200 mg/L for preparing unit doses. The freeze dried matrices may be sealed in a blister-pack type mold in which they were produced, as described above, or they may be placed in a nebulizer reservoir and sealed therein.

EXAMPLE 2

Twenty grams of acacia is placed in a dry 1L flask and about 10 mL of absolute alcohol is added. The flask is shaken to wet the acacia powder, and 500 mL of distilled water is introduced and shaken to yield a homogeneous solution. Thirty grams of polyvinylpyrrolidine and 1 g of R,R-formoterol -L-tartrate are dispersed into the solution with the aid of ultrasonic vibration. The final volume is adjusted to 1L with distilled water and 1 mL of the composition is added to each container (for multiple doses) or 20 to 50 $\mu$L is added to each container (for a unit dose). The lyophilization is carried out as described above. The container is then sealed with a pealable seal.

EXAMPLE 3

A hydrolyzed gelatin solution is prepared as in example 1. One gram of R,R-formoterol tartrate is dissolved in the solution. The final volume is adjusted to 1L with distilled water and 2 mL of the composition is added Rio a two-chamber container. The lyophilization is carried out as described above. The two-chamber vial is then sealed with a water impermeable seal.

The matrices prepared according to example 1 may be provided to the user as a component of a kit. The other component of the kit is a container containing the appropriate amount of buffered saline, or other suitable aqueous vehicle, sufficient to dissolve a single matrix (wafer) and provide a sterile, homogenous solution of precisely controlled concentration. Thus, for example, a wafer may contain 20–50 $\mu$g of R,R-formoterol tartrate, which is the range for one unit dose for inhalation. In that case, the second container may contain 2 mL of saline. The second container containing the saline may be a sealed nebulizer reservoir. In use, the wafer would be transferred from its sealed blister pack into a nebulizer reservoir and combined with the saline components. The wafer dissolves within seconds and provides the solution for a single inhalation session.

Alternatively, matrices may be prepared in accordance with example 2, wherein the container in which the solution is lyophilized is a reservoir for use in a nebulizer. The kit would then comprise the matrix in a sealed nebulizer reservoir as the first component and a container containing the appropriate amount of buffered saline, or other suitable aqueous vehicle, sufficient to dissolve the matrix as the other container. Similarly, the matrices may be prepared in accordance with example 1, placed in the nebulizer reservoir and sealed. In either case, addition of the saline to the reservoir provides a sterile, homogenous solution. The second container may contain 5–10 mL of saline.

Nebulizers and reservoirs suitable for the practice of this invention are commercially available from PARI Respiratory Equipment, Midlothian, Va. A schematic diagram of such a device is shown in FIG. 1, in which 2 is the inspiratory valve cap, 4 is the nebulizing chamber, 6 is the reservoir, 8 is the source of gas (air) and 10 is the mouthpiece. The reservoir is sealed at the top, at the air inlet 8 and at the mouthpiece orifice 9 with pealable seals 12, 14 and 18, and contains the lyophilized matrix 16. In use, the patient would remove the seals 12, 14 and 18, add the saline from the second container (not shown) and insert the chamber 4 with valve 2 attached into the reservoir 6.

In another embodiment, the matrix is created in a two-chambered container, as described in example 3. The container is a modification of the container described in U.S. Pat. Nos. 3,464,414; 4,331,233; 4,274,543; 4,267,925; 4,258,845; 4,194,640 and 4,089,432; the disclosures of which are incorporated herein by reference. The container 20 is shown in FIG. 2. The container is manufactured in an hourglass shape and a deformable elastomeric seal 22 is positioned in the neck. The matrix 16 is deposited on one side of the elastomeric seal and the aqueous vehicle (usually saline) 24 is placed on the opposite side. The container is closed at one end with a closure 26 having the structure described in the above patents. The closure is provided with a water and microorganism-tight seal such that the stopper 36 may be displaced and the elastomeric seal 22 can thereby be urged out of contact with the walls of the neck 30 of container 20, allowing the saline to enter the second chamber 32 in which the matrix resides. The chamber 32 containing the matrix is itself provided with a valve 34. The valve is of the type commonly employed in metered dose dispensers such as that sold by Aerogen, Inc., Santa Clara, Calif. and described in U.S. Pat. No. 5,586,550, the disclosure of which is incorporated herein by reference.

The use of the dual chamber vial in an Aerogen™ metered dose nebulizer is shown in FIG. 3. In operation, the stopper would be depressed by the user as described above, to generate the aqueous solution of medicament, and the dual chamber vial 20 would be inserted into the device 40, in which the oscillator described in U.S. Pat. No. 5,586,550 is 42. Also shown are the batteries 44, the circuit board 46, the acoustic inhalation detector 48 and the mouthpiece 50.

Although this invention is susceptible to embodiment in many different forms, preferred embodiments of the invention have been shown. It should be understood, however, that the present disclosure is to be considered as an exemplification of the principles of this invention and is not intended to limit the invention to the embodiments illustrated.

What is claimed is:

1. A pharmaceutical kit for aerosol administration of a medicament, said kit comprising:
   (a) a first substantially water-impermeable container containing a solid state open matrix network comprising a medicament and a pharmaceutically acceptable water soluble or water-dispersible carrier material; and
   (b) a second substantially water-impermeable container containing a sufficient quantity of an aqueous vehicle to dissolve said solid state open matrix network within fifteen seconds.

2. A kit according to claim 1 wherein said first container containing said solid state network and said second container containing said vehicle are separate.

3. A kit according to claim 1 wherein said first container containing said solid state network and said second container containing said vehicle are chambers within a single housing.

4. A kit according to claim 1 wherein said medicament is formoterol tartrate.

5. A kit according to claim 1 wherein said medicament is R,R-formoterol-L-tartrate.

6. A kit according to claim 1 wherein said pharmaceutically acceptable water soluble or water-dispersible carrier material is a protein, polypeptide or polysaccharide.

7. A kit according to claim 1 wherein said solid state network is a unit dose of said medicament and said quantity of aqueous vehicle is a quantity needed to deliver one unit dose by nebulization.

8. A kit according to claim 1 wherein said solid state network contains a plurality of unit doses of said medicament and said quantity of aqueous vehicle is a quantity needed to deliver said plurality of unit doses by nebulization.

9. A kit according to claim 8 additionally comprising a metered dose nebulizer.

10. A pharmaceutical kit for aerosol administration of a medicament, said kit comprising a nebulizer reservoir containing a solid state open matrix network comprising a medicament and a pharmaceutically acceptable water soluble or water-dispersible carrier material, said solid state open matrix network enclosed by a substantially water-impermeable seal, said seal being penetrable by a patient prior to use of said nebulizer reservoir.

11. A kit according to claim 10 wherein said solid state network contains a plurality of unit doses of said medicament.

12. A kit according to claim 10 wherein said medicament is formoterol tartrate.

13. A kit according to claim 10 wherein said medicament is R,R-formoterol-L-tartrate.

14. A method for preparing an aerosol formulation comprising:
   (a) providing a solid state open matrix network comprising a medicament and a pharmaceutically acceptable water soluble or water-dispersible carrier material; and
   (b) combining said matrix network with a sufficient quantity of an aqueous vehicle to dissolve said matrix network within fifteen seconds.

15. A method according to claim 14 wherein said open matrix network is a network of formoterol tartrate and a pharmaceutically acceptable water soluble or water-dispersible carrier material.

16. A method according to claim 14 wherein said open matrix network is a network of R,R-formoterol-L-tartrate and a pharmaceutically acceptable water soluble or water-dispersible carrier material.

17. A method for administering a water-sensitive medicament as a nebulized aqueous aerosol comprising:
   (a) dissolving a solid state open matrix network comprising a medicament and a pharmaceutically acceptable water soluble or water-dispersible carrier material in a sufficient quantity of an aqueous vehicle to dissolve said matrix network within fifteen seconds to provide an aqueous solution of the medicament and the carrier; and
   (b) nebulizing said aqueous solution.

18. A method according to claim 17 wherein said medicament is formoterol tartrate.

19. A method according to claim 17 wherein said medicament is R,R-formoterol-L-tartrate.

20. A method for providing a water-sensitive medicament for inhalation comprising:
   (a) dissolving or suspending a water-sensitive medicament and a pharmaceutically acceptable water soluble or water-dispersible carrier material in a vehicle;
   (b) introducing said medicament, carrier and vehicle into a reservoir for a nebulizer;
   (c) freezing said medicament, carrier and vehicle in said reservoir; and
   (d) lyophilizing said medicament, carrier and vehicle in said reservoir to provide a solid state open matrix network comprising said medicament and carrier in said reservoir.

21. A method according to claim 20 wherein said medicament is formoterol tartrate.

22. A method according to claim 20 wherein said medicament is R,R-formoterol-L-tartrate.

* * * * *